US009370339B2

(12) United States Patent
Hazard et al.

(10) Patent No.: US 9,370,339 B2
(45) Date of Patent: Jun. 21, 2016

(54) SYSTEMS, METHODS AND COMPUTER PROGRAMS FOR DETECTION OF TISSUE MECHANICAL PROPERTY

(71) Applicant: General Electric Company, Schenectady, NY (US)

(72) Inventors: Christopher Robert Hazard, Niskayuna, NY (US); Wei Tan, Shanghai (CN); Xiaodong Han, Shanghai (CN); Gang Cheng, Shanghai (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 182 days.

(21) Appl. No.: 13/804,750

(22) Filed: Mar. 14, 2013

(65) Prior Publication Data
US 2013/0245442 A1    Sep. 19, 2013

(30) Foreign Application Priority Data

Mar. 16, 2012  (CN) .......................... 2012 1 0071055

(51) Int. Cl.
*A61B 8/08*   (2006.01)
*A61B 8/00*   (2006.01)
*G01S 7/52*   (2006.01)

(52) U.S. Cl.
CPC ............... *A61B 8/485* (2013.01); *A61B 8/4483* (2013.01); *A61B 8/54* (2013.01); *G01S 7/52036* (2013.01); *A61B 8/5223* (2013.01); *G01S 7/52042* (2013.01)

(58) Field of Classification Search
CPC .... A61B 8/485; A61B 8/0825; A61B 8/4483; A61B 8/4488; G01S 7/2042

USPC ......................................................... 600/438
See application file for complete search history.

(56) References Cited

U.S. PATENT DOCUMENTS

| 2007/0038095 | A1  | 2/2007  | Greenleaf et al. |
| 2008/0249408 | A1* | 10/2008 | Palmeri et al. ................ 600/438 |
| 2010/0016718 | A1  | 1/2010  | Fan et al. |
| 2010/0286516 | A1  | 11/2010 | Fan et al. |

(Continued)

FOREIGN PATENT DOCUMENTS

| WO | 2011001333 A1 | 1/2011 |
| WO | 2011064688 A1 | 6/2011 |

OTHER PUBLICATIONS

Greenleaf et al., "Ultrasonic Viscoelastic Tissue Measurements", AccessScience, 2009.

(Continued)

*Primary Examiner* — Baisakhi Roy
(74) *Attorney, Agent, or Firm* — GE Global Patent Operation; Mark A. Vivenzio

(57) ABSTRACT

In accordance with embodiments disclosed herein, systems, methods, and computer programs are provided that determine a mechanical property of a subject. An excitation force is applied to a displacement origin within a subject, and a shear wave is generated in response to application of the excitation force. The displacement data indicative of displacement motion at the sample position is sampled by tracking pulses, and the timing of at least one of the tracking pulses is adjusted relative to application of the excitation force. The process continues until a peak displacement of the shear wave for the sample position is determined based upon the displacement data.

22 Claims, 7 Drawing Sheets

(56) References Cited

U.S. PATENT DOCUMENTS

| | | |
|---|---|---|
| 2010/0317971 A1 | 12/2010 | Fan et al. |
| 2011/0063950 A1 | 3/2011 | Greenleaf et al. |
| 2011/0066030 A1 | 3/2011 | Yao et al. |
| 2011/0263978 A1 | 10/2011 | Chen et al. |
| 2011/0319756 A1 | 12/2011 | Zheng et al. |
| 2013/0131511 A1* | 5/2013 | Peterson et al. ............. 600/438 |

OTHER PUBLICATIONS

McAleavey et al., "Shear Modulus Imaging with Spatially Modulated Ultrasound Radiation Force", Ultrason Imaging, vol. 31, Issue 4, pp. 217-234, Oct. 2009.

Unofficial English Translation of Chinese Office Action and Search Report issued in connection with corresponding CN Application No. 201210071055.2 on Aug. 26, 2014.

* cited by examiner

SYSTEMS, METHODS AND COMPUTER PROGRAMS FOR DETECTION OF TISSUE MECHANICAL PROPERTY

BACKGROUND TO THE INVENTION

Mechanical properties of tissue have important use in medical applications because these properties are closely linked to tissue state with respect to pathology. For example, measurement of liver stiffness can be used as a non-invasive alternative for liver fibrosis staging. Recently, ultrasound imaging was developed to measure mechanical properties of tissues. Typically, an ultrasound transducer fires a long duration, focused ultrasound pulse to a displacement origin to induce a displacement motion within a tissue of interest. As a result of this displacement motion, a shear wave propagates outwards from the displacement origin. Tissue mechanical properties can be determined by detecting this shear wave. For example, a time to peak displacement for two or more sample positions with known distance along the propagation path is detected to measure a shear wave velocity. Using the shear wave velocity, tissue mechanical properties can be calculated.

To detect the peak displacement, a temporal displacement for each sample position is measured by repeatedly transmitting ultrasound pulses to and receiving echo signals from the sample position. In conventional peak displacement detection, pulse repetition frequency (PRF) of the ultrasound pulses defines a sampling rate of the temporal displacement measurement and directly affects the accuracy of the peak displacement detection. As transmission of a new ultrasound pulse has to occur after echoes in response to the previous ultrasound pulse have been received from the depth of interest, the PRF cannot be readily increased to improve the sampling rate. The limited sampling rate impedes conventional ultrasound systems to perform peak displacement detection accurately.

BRIEF DESCRIPTION OF THE INVENTION

In accordance with embodiments of the present invention disclosed herein, systems, methods, and computer program products are provided that determine a mechanical property of a subject. In an embodiment, a method for applying an excitation force to a displacement origin within a subject, and generating a shear wave in response to application of the excitation force is disclosed herein. The method further comprises sampling a plurality of displacement data indicative of displacement motion at a sample position by a plurality of tracking pulses, and adjusting a timing of at least one of the tracking pulses relative to application of the excitation force. The method repeats until a peak displacement of the shear wave for the sample position is determined based upon the displacement data.

In an embodiment of the present invention, a system comprising an ultrasound transducer is disclosed. The ultrasound transducer performs a pushing tracking event pair, which comprises applying an excitation force to a displacement origin within a tissue to generate a shear wave in the pushing event and sampling a plurality of displacement data indicative of displacement motion of the tissue at a sample position by a plurality of tracking pulses in the tracking event. The system further comprises a memory for storing the displacement data and program instructions as well as a processor for executing the program instructions to control the ultrasound transducer. The ultrasound transducer performs at least one occurrence of the pushing tracking event pair for the sample position with an adjusted timing of the tracking pulses relative to application of the excitation force in each occurrence until a peak displacement of the shear wave for the sample position is determined based upon the displacement data.

In an embodiment, a non-transitory computer readable media comprising program instructions, which when executed by one or more processors measure a shear wave velocity in a tissue with an ultrasound system is disclosed. The program instructions comprise repeating a plurality of steps until one of displacement data indicative of displacement motion of the tissue at a sample position is determined as a peak displacement of the shear wave. Each repetition of the steps comprises applying a pushing pulse to a displacement origin within the tissue, generating the shear wave in response to the pushing pulse, sampling the displacement data by a plurality of tracking pulses, and adjusting a timing of at least one of the tracking pulses relative to the pushing pulse. The program instructions further comprise calculating the shear wave velocity based upon the peak displacement.

BRIEF DESCRIPTION OF THE DRAWINGS

These and other features and aspects of embodiments of the present invention will become better understood when the following detailed description is read with reference to the accompanying drawings in which like characters represent like parts throughout the drawings, wherein.

DETAILED DESCRIPTION OF THE INVENTION

Figure 1:
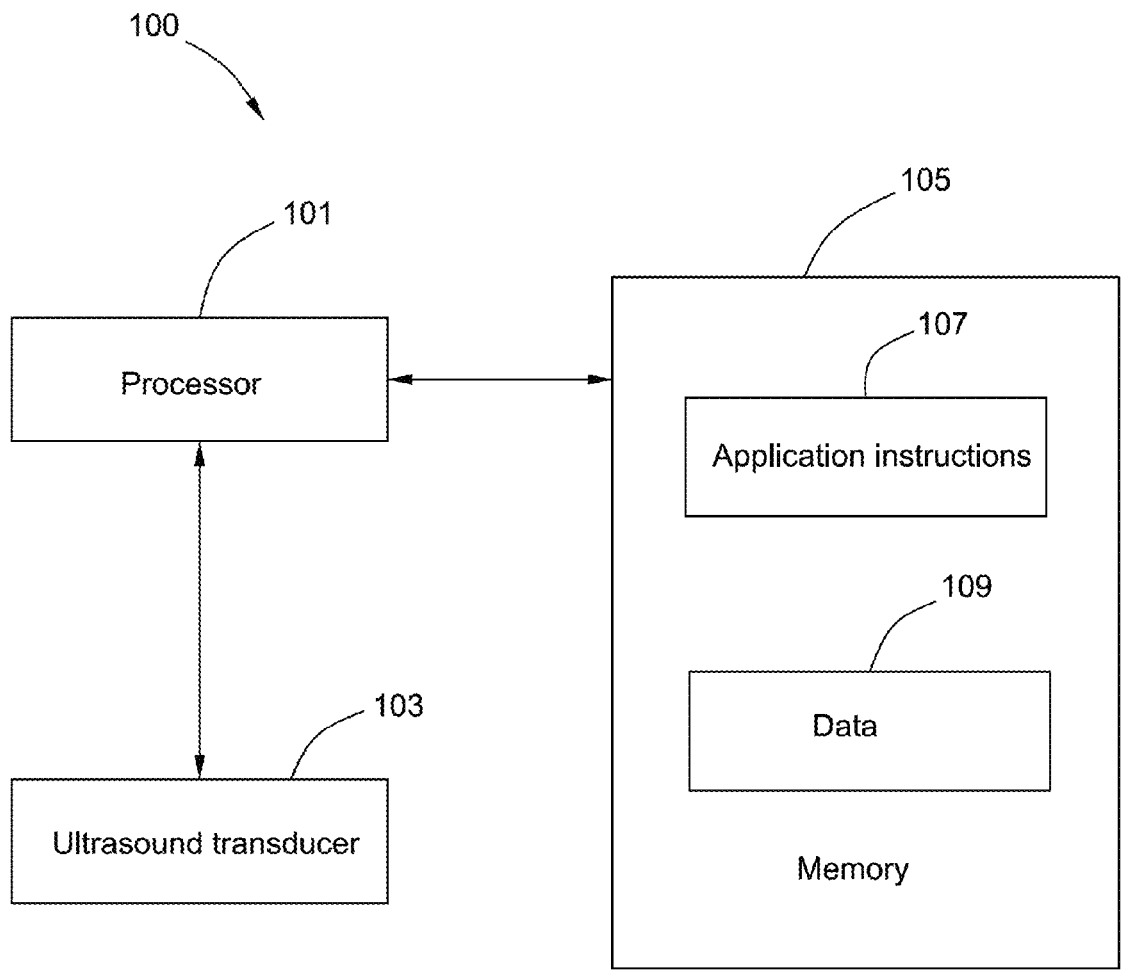
FIG. 1 is a block diagram of an ultrasound system according to an embodiment of the present invention.

Embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Unless defined otherwise, technical and scientific terms used herein have the same meaning as is commonly understood by one of ordinary skill in the art to which this disclosure belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced items. The use of "including", "comprising", or "having" and variations thereof herein are meant to encompass the items listed thereafter and equivalents thereof as well as additional items. The terms "connected" and "coupled" are not restricted to physical or mechanical connections or couplings, and can include electrical connections or couplings, whether direct or indirect.

As discussed in detail below, exemplary embodiments disclosed herein relate to an ultrasound system with the capability of detecting a mechanical property of a subject. More specifically, a detection process is developed for the ultrasound system to determine a peak location of a shear wave for two or more sample positions. Based on the peak location for the sample positions, the mechanical property of the subject is calculated according to various methods, such as a level tracking method and a time to peak displacement method. According to an embodiment of the detection process, the ultrasound system repeats the steps of applying a pushing pulse to a displacement origin within the subject, generating a shear wave in response to the pushing pulse, sampling displacement data indicative of displacement motion of the subject in response to the shear wave by tracking pulses, and adjusting a timing of at least one of the tracking pulses relative to the pushing pulse. The detection process proceeds until a respective displacement data is determined as a peak displacement of the shear wave for a respective sample position. As the peak displacement for each sample position is located, a mechanical property of the subject can be calculated. For example, the time to peak displacement is recorded and used to calculate the mechanical property of the subject, such as tissue shear modulus, tissue shear viscosity, tissue shear velocity and tissue elasticity.

FIG. 1 is a block diagram of an ultrasound system 100 in accordance with an embodiment of the present invention. Detailed descriptions of well-known functions, configurations or constructions are omitted for brevity and clarity so as not to obscure the description of the present disclosure with unnecessary detail. Thus, the present invention is not limited to the exemplary embodiments which will be described below, but may be implemented in other forms. The ultrasound system 100 includes a processor 101, an ultrasound transducer 103, and a memory 105. The memory 105 includes an application instructions module 107 and a data module 109. The ultrasound transducer 103 interacts with a subject, for example a biological tissue, to sample displacement data indicative of displacement motion of the subject at two or more sample positions. The displacement data is stored into the data module 109 through I/O devices (not shown) within the ultrasound system 100. The application instructions module 107 includes software routines that implement the functionality of the ultrasound system 100 when executed by the processor 101, for example to determine a mechanical property of the subject.

Figure 2:
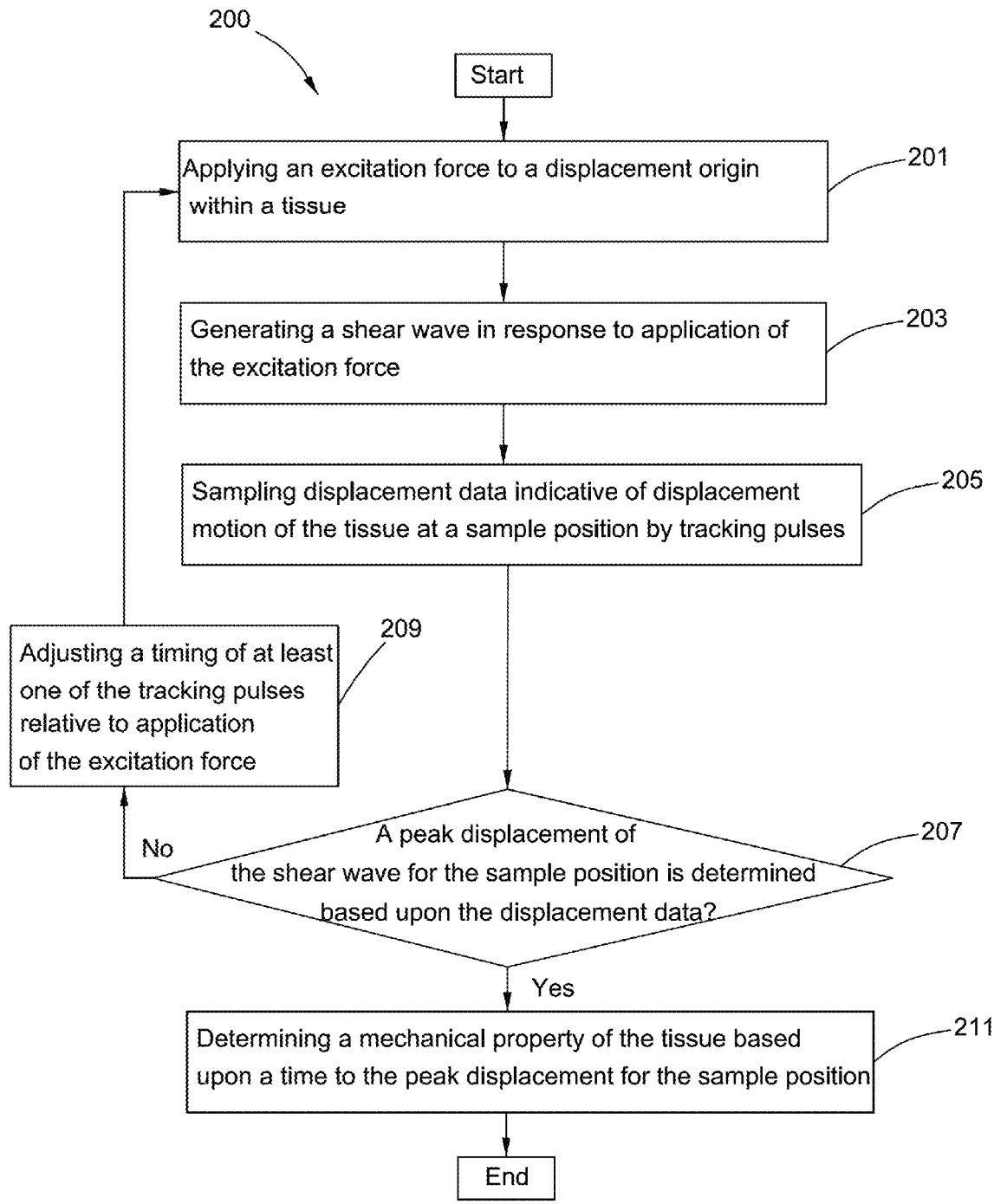
FIG. 2 is a flow chart diagram of a method for determining a mechanical property of a subject with the ultrasound system in FIG. 1 according to an embodiment of the present invention.

FIG. 2 is a flow chart diagram 200 illustrating example operations of the ultrasound system 100 as the software routines residing in the application instructions modules 107 are executed by the processor 101. More specifically, FIG. 2 illustrates operations pertaining to measurement of tissue mechanical property using an exemplary detection process. FIG. 2 is described in combination with FIG. 1.

The detection process starts with step 201, where a first occurrence of a pushing event initiates as an excitation force is applied to a displacement origin within a tissue. In an embodiment, the excitation force is produced by radiation pressure from an ultrasound pulse. For example, the ultrasound transducer 103 fires a long duration, focused pushing pulse to the displacement origin to generate the excitation force. In other embodiments, the excitation force is produced by pressure from various sources, such as manual pressure and an external vibration source. In response to application of the excitation force, the tissue at the displacement origin is compressed downward. Once the excitation force is released, the tissue at the displacement origin rebounds back up. Since the compressed tissue at the displacement origin is joined to surrounding tissue, the uncompressed tissue surrounding in the lateral direction will respond to the up-and-down movement of the compressed tissue. As such, in response to application of the excitation force, a shear wave referring to a ripple effect of the uncompressed tissue surrounding the displacement origin in the lateral direction is generated at step 203. At step 205, the ultrasound transducer 103 performs a first occurrence of a tracking event by applying tracking pulses to a sample position. The tracking pulses sample displacement data indicative of displacement motion at the sample position as the shear wave propagates through the tissue.

Through operations of steps 201 to 205, the ultrasound transducer 103 completes a first occurrence of pushing tracking event pair. At step 207, the processor 101 determines whether the peak displacement of the shear wave is located. If the peak displacement of the shear wave is not located, the processor 101 adjusts a timing of at least one of the tracking pulses relative to application of the excitation force for the next occurrence at step 209, and the next occurrence of the pushing tracking event pair begins by executing step 201. Otherwise, the occurrence of the pushing tracing event pair terminates. The timing adjustment at step 207 causes samplings from different occurrences of the pushing tracking event pair to differ from each other so as to obtain more sample points demonstrating a temporal displacement motion of the shear wave at the sample position. By doing so, although with the limitation of relatively low PRF of tracking pulses, the effective sampling rate of the shear wave is increased. In an embodiment of peak displacement detection where a peak displacement of the shear wave is estimated using the sampled displacement data at step 205, high sampling rate improves the precision of the peak displacement detection. Moreover, in an embodiment, the timing adjustment at step 209 enables a maximum value of the displacement data to move towards the peak displacement of the shear wave as the occurrence of the pushing tracking event pair proceeds. More particularly, by estimating the peak location from a pushing tracking event pair and adjusting the timing for a future pushing tracking event pair, the peak region is captured more effectively. As such, one of the sampled displacement data can be ultimately determined as the peak displacement of the shear wave at step 207. In this embodiment, the precision of the peak displacement detection is further enhanced as compared to estimating the peak displacement using the displacement data.

In an embodiment, two or more sample positions displaced along the propagation path of the shear wave are detected for the peak displacement. Once the peak displacement is detected for these sample positions, the mechanical property of the tissue, such as tissue shear modulus, tissue shear viscosity, tissue shear velocity and tissue elasticity, can be calculated according to various methods. In an embodiment, the processor 101 determines the mechanical property of the tissue based on time to the peak displacement for the sample positions at step 211.

Figure 3:
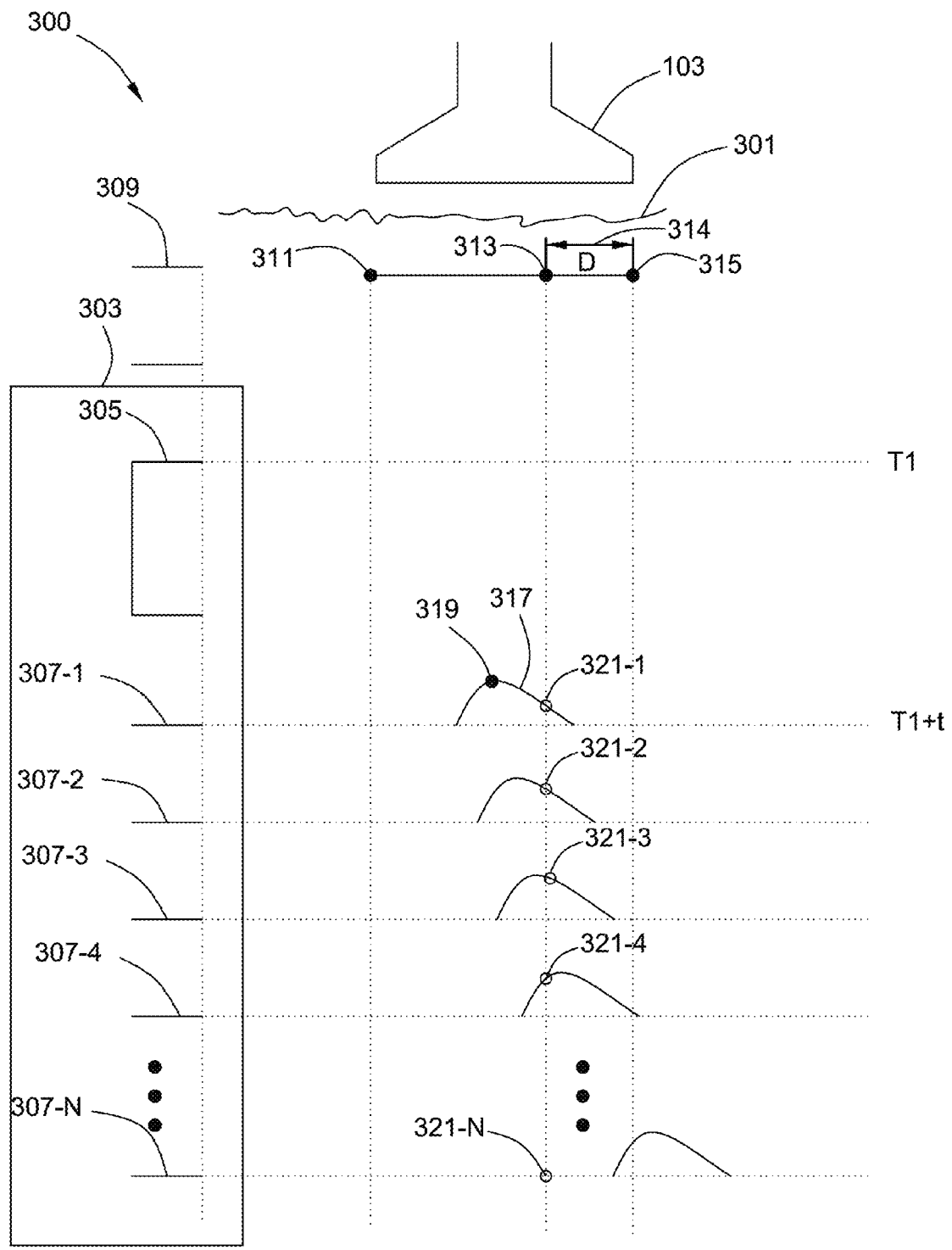
FIG. 3 is an example graphical representation of spatial shear wave displacement as the shear wave propagates through a subject according to an embodiment of the present invention.
Figure 4:
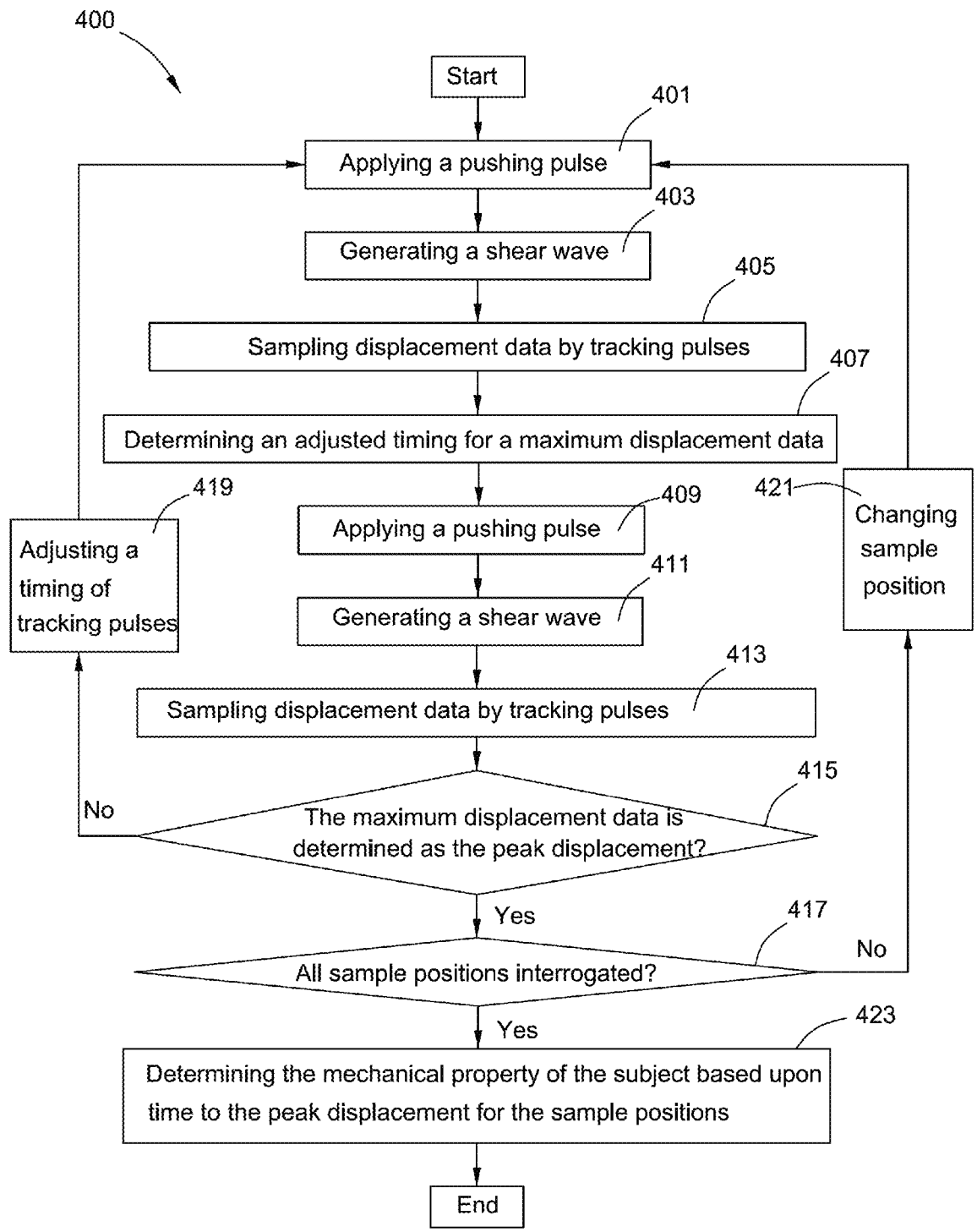
FIG. 4 is a flow chart diagram of a method for determining a mechanical property of the subject in FIG. 3 according to an embodiment of the present invention.
Figure 5:
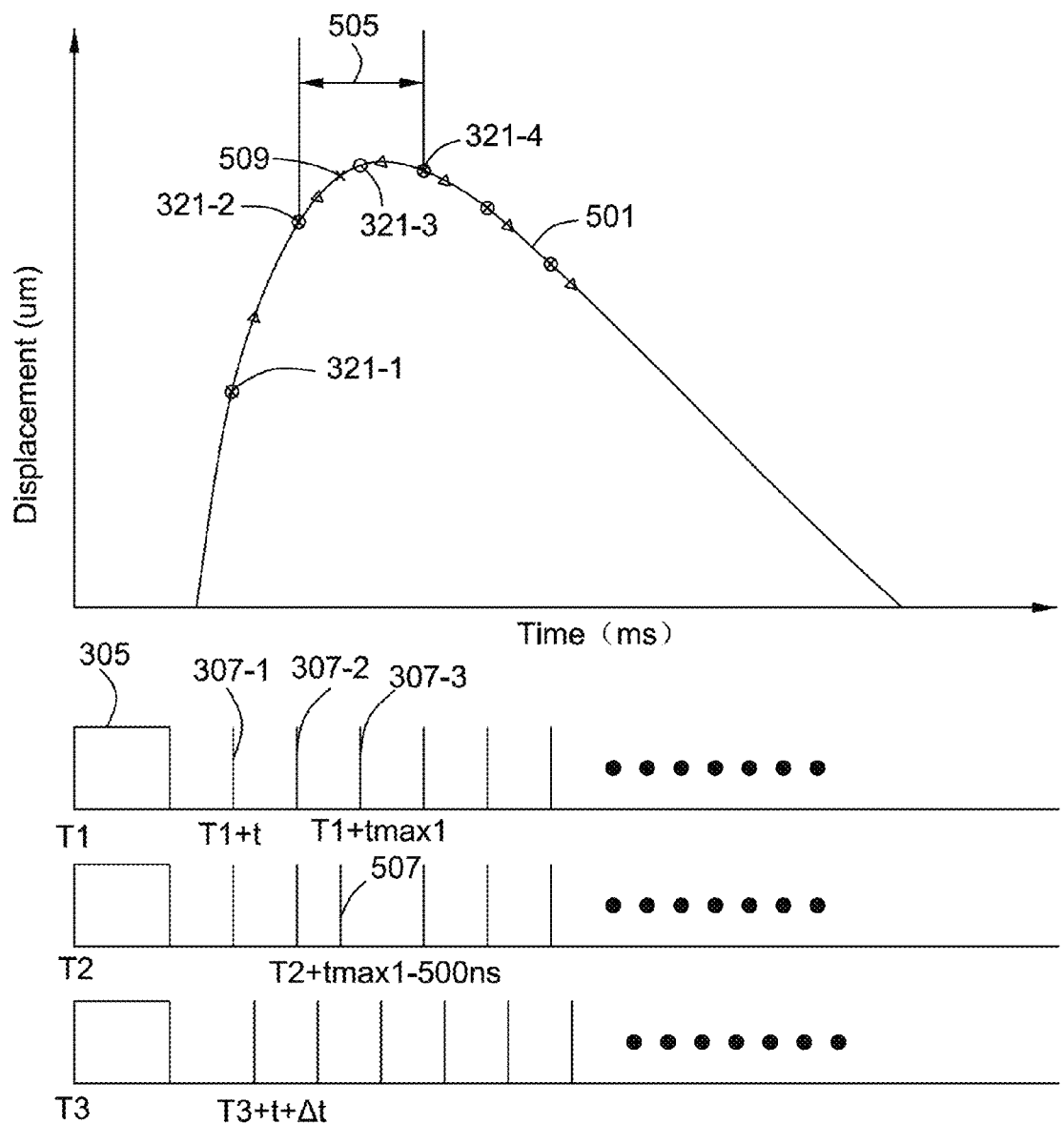
FIG. 5 is an example sampling of a temporal shear wave displacement at a sample position according to the operation in FIG. 4.

FIG. 3 is a graphical representation 300 of spatial shear wave displacement illustrating shear wave propagation in a subject as a function of time in accordance with an embodiment. FIG. 4 illustrates a flow chart diagram 400 of operations for measuring a mechanical property of the subject in FIG. 3 in accordance with an embodiment. FIG. 5 illustrates samplings of a temporal shear wave displacement at a sample position resulting from the operations in FIG. 4. FIGS. 3, 4 and 5 are described in combination.

Referring to FIGS. 3 and 4, the ultrasound transducer 103 fires ultrasound pulses in a timing sequence 303 to a subject 301 in an occurrence of pushing tracking event pair. At step 401, the transducer 103 initiates a first occurrence of the pushing event by applying a pushing pulse 305 to a displacement origin 311 at time T1. In response, a shear wave 317 is induced and propagates outwards from the displacement origin 311 at step 403. Once a peak displacement 319 of the shear wave 317 is detected at two or more sample positions along the propagation path, for example sample positions 313 and 315, time to peak displacement $T_{PEAK1}$ and $T_{PEAK2}$ for the sample positions 313 and 315 are recorded, respectively. Assuming a distance 314 between sample positions 313 and 315 is D, shear wave velocity $C_S$ can be given according to equation (1), $$C_S = D/(T_{PEAK2} - T_{PEAK1}) \quad (1).$$

With more sample positions, a more accurate average of shear wave velocity $C_S$ is achieved. Using the shear wave velocity $C_S$, the mechanical property of the subject 301, such as shear modulus, shear viscosity, and elasticity of the subject, can be calculated accordingly.

As an example of peak displacement detection for the sample position 313, the transducer 103 initiates a first occurrence of the tracking event by firing tracking pulses 307-1 to 307-N to the sample position 313 from time T1+t at step 405. Corresponding to the tracking pulses 307-1 to 307-N, sample points 321-1 to 321-N are obtained to demonstrate a temporal shear wave displacement at the sample position 313 as the shear wave 317 travels outwards from the displacement origin 311. Referring also to FIG. 5, a temporal shear wave displacement curve 501 for the sample position 313 is shown together with the sample points 321-1 to 321-N marked with "O". Displacement data associated with each sample point indicates displacement magnitude experienced by the sample position 313 at the corresponding sampling time. In an embodiment, the displacement data is detected through a pulse-echo process. As an example of the pulse-echo process, prior to application of the pushing pulse 305, a reference pulse 309 is transmitted to the sample position 313 and echo signals resulting from the reference pulse 309 contain reference data for displacement estimation. As the tracking pulses 307-1 to 307-N are transmitted, phases of echo signals resulting from the tracking pulses 307-1 to 307-N are measured relative to the reference data to obtain the displacement data for the sample position 313.

Referring back to FIG. 4, at steps 407, an adjusted timing of tracking pulses relative to the pushing pulse is determined for a second occurrence of pushing tracking event pair. At step 409, a pushing pulse substantially identical to that in the first occurrence is applied to the displacement origin 311 at time T2 to start the second occurrence. At step 411, the shear wave is generated. At step 413, tracking pulses are fired to the sample position 313 according to the adjusted timing to sample displacement data in the second occurrence. For example, sample points in the second occurrence are marked with "x" in FIG. 5.

The timing adjustment associated with step 407 is described in detail with reference to FIG. 5. As an example, a sample point 321-3 having the maximum displacement data in the first occurrence is sampled by a tracking pulse 307-3 fired at time T1+$t_{max1}$. A time interval between sample points 321-2 and 321-4 left and right adjacent to the sample point 321-3 defines a peak detection window 505 for the sample position 313. The tracking pulses in the second occurrence are determined to obtain a new maximum displacement data close to the maximum displacement data in the first occurrence and within the peak detection window 505. To the end, a timing of the tracking pulse 307-3 corresponding to the maximum displacement data in the first occurrence is used to determine a timing of a tracking pulse corresponding to a maximum displacement data in the second occurrence. As shown in FIG. 5, a sample point 509 with the maximum displacement data in the second occurrence is sampled by a tracking pulse 507. The timing of the tracking pulse 507 relative to the pushing pulse fired at time T2 is determined by shifting the tracking pulse 503 left in time by 500 ns relative to the pushing pulse fired at time T1. That is, the tracking pulse 507 is fired at time T2+$t_{max1}$−500 ns to sample the maximum displacement data in the second occurrence.

The difference between the maximum displacement data in the first and second occurrences provides estimation for slope K of the shear wave. The slope K is given by an equation (2)

$$K = (A_{ITE1} - A_{ITE2})/T_d \quad (2),$$

where $A_{ITE1}$ is the maximum displacement data sampled in the first occurrence, $A_{ITE2}$ is the maximum displacement data sampled in the second occurrence, and $T_d$ is the shifted time interval between tracking pulses corresponding to the maximum displacement data in the first and second occurrences. In the example of FIG. 5, the slope K is equal to a displacement difference between sample points 321-3 and 509 divided by the shifted time interval 500 ns. In an embodiment, except for the tracking pulse 507, the timing of the tracking pulses relative to the pushing pulse in the second occurrence is the same as those in the first occurrence so as to estimate a low frequency drift between the first and second occurrences. The maximum displacement data of the sample point 509 is corrected for the drift. In other embodiments, more than one tracking pulses around the tracking pulse 507 can be shifted together to obtain the slope K.

Referring back to FIG. 4, at step 415, the displacement data of the sample point 321-3 is evaluated to determine whether it is the peak displacement for the sample position 313. In an embodiment, if the slope K is greater than a predetermined threshold, the sample point 321-3 is not determined as the peak displacement. As such, the flow chart 400 goes to step 419 to determine a timing of tracking pulses in a third occurrence. In this instance, the timing shift direction is determined by a sign of the slope K. In the example of FIG. 5, the slope K has a positive sign, which indicates the peak displacement for the sample position 313 is located between the sample point 321-3 and 321-4. To move the maximum displacement data sampled in the third occurrence towards the peak displacement, tracking pulses in the third occurrence are shifted right from tracking pulses in the first iteration by a step interval ΔT. In an embodiment, the step interval ΔT is given by an equation (3)

$$\Delta T = K1 * K \quad (3),$$

where K1 is a step constant. Alternatively, the step interval $\Delta T$ is determined based on a pulse repetition time (PRT), which is the reciprocal of the PRF, for example, half of PRT. In other embodiments, a function, such as a parabola or a polynomial, can be acquired based on the displacement data to estimate the step interval $\Delta T$.

Once the adjusted timing for the third occurrence is determined, the flow chart 400 returns to steps 401 to 405 to complete the third occurrence according to the adjusted timing. In the exemplary third occurrence of FIG. 5, the pushing pulse is fired at time T3 and the tracking pulses are fired from time T3+t+$\Delta T$. All tracking pulses in the third occurrence are time shifted as compared to the tracking pulses in the first occurrence. Sample points in the third occurrence are marked with "$\Delta$". Alternatively, a part of the tracking pulses, for example, the tracking pulses associated with the sampling points defining the peak detection window 505, are time shifted while the timing of remaining pulses is kept the same. As discussed above, sample points tracked by tracking pulses with the same timing from different iteration are used to correct the maximum displacement data for the low frequency drift.

From step 405 on, the detection process for the sample position 313 repeats as discussed above until one of the displacement data is determined as the peak displacement at step 415, for example, when the slope K is less than the predetermined threshold. Once the detection process for the sample position 313 ends, the sample position 315 is interrogated at step 417. Through changing the sample position at step 421, the peak displacement detection for the sample position 315 begins. If there are more sample positions, the peak displacement detection for these sample positions can be performed in a similar manner. As discussed in relation to FIG. 3, the shear wave velocity is calculated based on time to peak displacement for two or more sample positions with known distance. At step 423, the mechanical property of the subject, such as shear modulus, shear viscosity, shear velocity of the subject, is calculated using the shear wave velocity. Moreover, the detection process is also beneficial to other methods relating to subject mechanical property calculation, such as the level tracking method.

In reference to embodiments discussed with reference to FIGS. 3, 4 and 5, the time T2 for firing the pushing pulse in the second occurrence can be prior to or after the time T1+t for firing the tracking pulses in the first occurrence. That is, a pushing tracking event pair can occur after displacement from a previous pushing tracking event pair recovers to zero in an embodiment. In an alternative embodiment, the pushing tracking event pairs overlap by firing two or more pushing pulses successively prior to firing the tracking pulses. Overlapping the pushing tracking event pairs is advantageous due to reduced effect of background noise and enhanced energy efficiency.

In addition, the two or more sample positions as discussed with reference to FIGS. 3, 4 and 5, can be sampled in different manners using focused tracking pulses, such as a single position manner, an interleaving position manner, and a sequential position manner. The operations in the single position manner are illustrated in FIG. 4, and accordingly the temporal shear wave displacement sampling shown in FIG. 5 is consistent with the operations in the single position manner. Alternatively, for transducers with multiline acquisition capability, a single unfocused tracking pulse is employed to sample multiple sample positions simultaneously. With minor variation, the steps in FIG. 4 are readily applicable to implementations with the interleaving position manner, the sequential position manner, or the multiline acquisition. For example, the steps 417 and 421 are not necessarily performed for the interleaving position manner, the sequential position manner, and the multiple acquisitions. These varied steps are in accordance with this disclosure.

Figure 6:
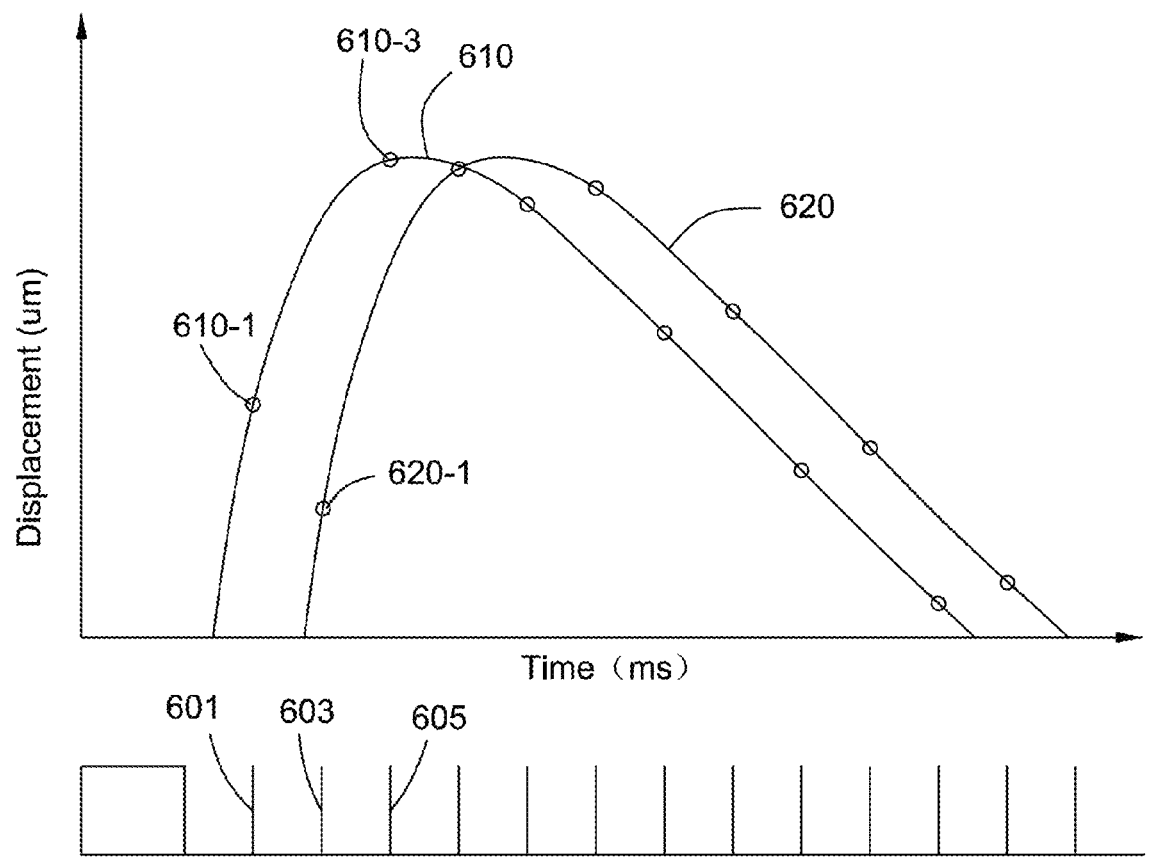
FIG. 6 is an example sampling of temporal shear wave displacement at two sample positions in an interleaving position manner according to an embodiment of the present invention.

With reference to FIG. 6, samplings of shear wave displacement for the sample positions 313 and 315 in the interleaving position manner are discussed. Sample points are marked with "O" in FIG. 6. As indicated by a shear wave displacement curve 610 for the sample position 313 and a shear wave displacement curve 620 for the sample position 315, the samplings for the sample positions 313 and 315 are time interleaved. In the embodiment shown in FIG. 6, a first tracking pulse 601 is fired to the sample position 313 to obtain the sample point 610-1, and the next tracking pulse 603 is fired to the sample position 315 to obtain the sample point 620-1. Then, the sample position 313 is sampled again by the tracking pulse 605 to obtain the sample point 610-3, and the sequence repeats. Since the sampling is time interleaved, each of the sample positions is sampled once in every N tracking pulses in this example, where N is equal to the number of sample positions. In an embodiment, the sample positions can be grouped with each group having two or more sample positions. The sample positions within each group are sampled in the interleaving position manner and the groups are sampled one by one.

With more than one sample position sampled in an occurrence of the pushing tracking event pair, the interleaving position manner is more energy and time effective. Additionally, since the sample positions experience similar background noise with the same pushing pulse, the effect of background noise is further reduced.

Figure 7:
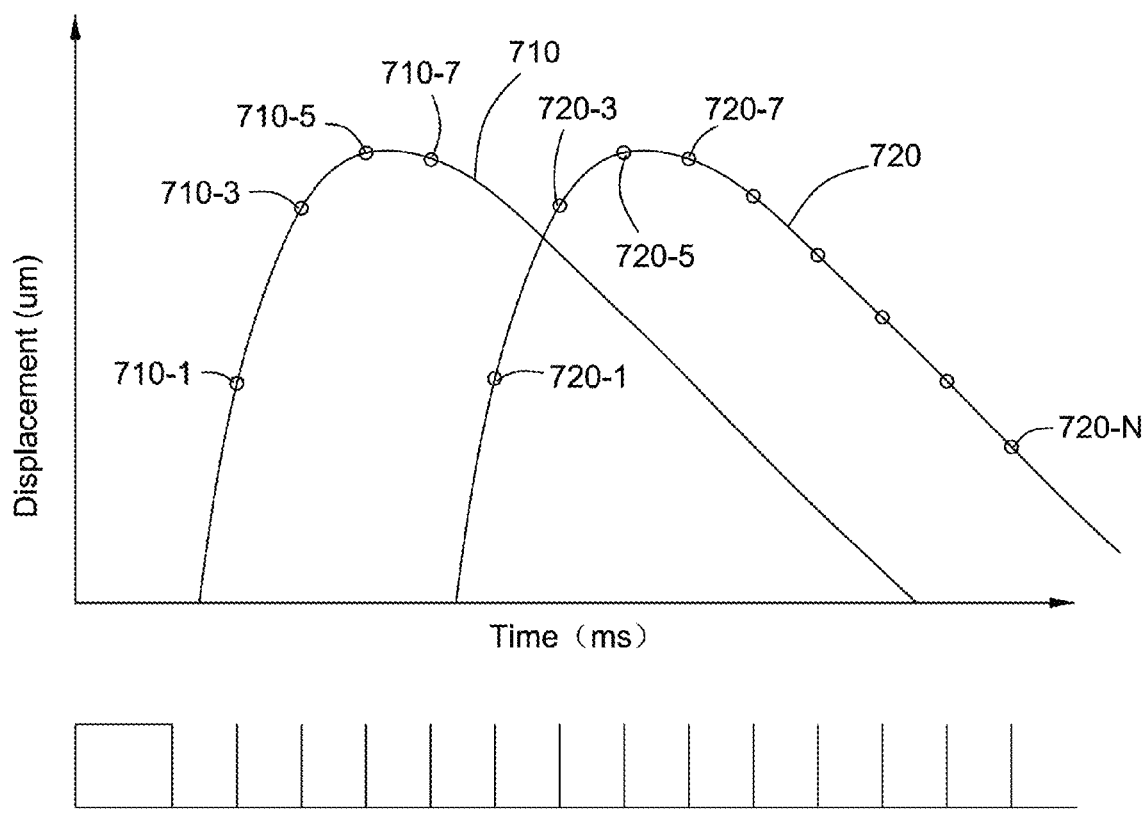
FIG. 7 is an example sampling of temporal shear wave displacement at two sample positions in a sequential position manner according to an embodiment of the present invention.

With reference to FIG. 7, samplings of shear wave displacement motion for the sample positions 313 and 315 in the sequential position manner are discussed. Sample points are marked with "O" in FIG. 7. As indicated by a shear wave displacement curve 710 for the sample position 313 and a shear wave displacement curve 720 for the sample position 315, the samplings for the sample positions 313 and 315 are conducted sequentially. In the example of FIG. 7, the first four tracking pulses are fired to the sample position 313 to obtain the sample points 710-1, 710-3, 710-5 and 710-7, and the following tracking pulses are fired to the sample position 315 to obtain the sample points 720-1 through 720-N. That is, each of the sample positions is allocated with several successive tracking pulses and the sample positions are shifted one by one. The number of tracking pulses allocated to each sample position is determined to ensure that the peak displacement at each sample position is experienced within a time period defined by corresponding tracking pulses. Similarly, the sequential position manner is advantageous in terms of time and energy efficiency and background noise effect.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method, comprising:
   applying an excitation force to a displacement origin within a subject;

generating a shear wave in response to application of the excitation force;

sampling displacement data indicative of displacement motion at a sample position by a plurality of tracking pulses;

adjusting a timing of at least one of the tracking pulses relative to application of the excitation force by causing samplings from different occurrences of the excitation force to differ from each other so as to obtain more sample points demonstrating a temporal displacement motion of the shear wave at the sample position; and repeating the applying, generating, sampling and adjusting steps until a peak displacement of the shear wave for the sample position is determined based upon the displacement data.

2. The method of claim 1, wherein applying the excitation force comprises applying an ultrasound pulse to the displacement origin.

3. The method of claim 1, wherein the excitation force is produced by a vibration source.

4. The method of claim 1, wherein adjusting the timing comprises adjusting the timing of the tracking pulses based upon a pulse repetition time of the tracking pulses.

5. The method of claim 1, wherein adjusting the timing comprises:

determining a first timing of a first tracking pulse corresponding to a first maximum displacement data; and adjusting a second timing of a second tracking pulse corresponding to a second maximum displacement data based upon the first timing.

6. The method of claim 5, further comprising:

determining a drift with the second maximum displacement data; and correcting the second maximum displacement data for the drift.

7. The method of claim 5, further comprising:

determining a slope of the shear wave based on the first and second maximum displacement data; and determining whether the first maximum displacement data is the peak displacement based upon the slope.

8. The method of claim 5, further comprising:

determining a timing shift direction of the tracking pulses based upon the first and second maximum displacement data.

9. The method of claim 8, wherein adjusting the timing comprises:

adjusting the timing of the tracking pulses in the timing shift direction based on the first and second maximum displacement data.

10. The method of claim 8, further comprising:

adjusting the timing of the tracking pulses in the timing shift direction based on a pulse repetition time of the tracking pulses.

11. The method of claim 1, further comprising:

determining a mechanical property of the subject based upon a time to the peak displacement for the sample position; and calculating a velocity of the shear wave based upon the time to the peak displacement for the sample position.

12. The method of claim 11, wherein the mechanical property of the subject is selected from the group consisting of shear modulus, shear viscosity, shear velocity and elasticity of the subject.

13. The method of claim 1, further comprising:

transmitting the tracking pulses to the sample position in a manner selected from the group consisting of a single position manner, an interleaving position manner, and a sequential position manner.

14. The method of claim 1, further comprising:

transmitting a reference pulse; and calculating the displacement data based upon echo signals in response to the reference pulse and echo signals in response to the tracking pulses.

15. A system, comprising:

an ultrasound transducer for performing a pushing tracking event pair, which comprises applying an excitation force to a displacement origin within a tissue to generate a shear wave in the pushing event and sampling a plurality of displacement data indicative of displacement motion of the tissue at a sample position by a plurality of tracking pulses in the tracking event;

a memory for storing the displacement data and program instructions; and a processor for executing the program instructions to control the ultrasound transducer to perform at least one occurrence of the pushing tracking event pair for the sample position with an adjusted timing of the tracking pulses relative to application of the excitation force in each occurrence until a peak displacement of the shear wave for the sample position is determined based upon the displacement data, wherein the processor is configured to adjust the timing of the tracking pulses by causing samplings from different occurrences of the pushing tracking event pair force to differ from each other so as to obtain more sample points demonstrating a temporal displacement motion of the shear wave at the sample position.

16. The system of claim 15, wherein the processor is configured to determine a mechanical property of the tissue based upon a time to the peak displacement and to calculate a velocity of the shear wave based upon the time to the peak displacement.

17. The system of claim 15, wherein the ultrasound transducer is configured to transmit the tracking pulses to the sample position in a manner selected from the group consisting of a single position manner, an interleaving position manner, and a sequential position manner.

18. The system of claim 15, wherein the timing of the tracking pulses is adjusted based on a pulse repetition time of the tracking pulses.

19. The system of claim 15, wherein the processor is configured to determine a previous timing of a previous tracking pulse corresponding to a previous maximum displacement data in a previous occurrence of the pushing tracking event pair and configured to adjust a current timing of a current tracking pulse corresponding to a current maximum displacement data in a current occurrence of the pushing tracking event pair based upon the previous timing.

20. The system of claim 19, wherein the processor is configured to determine whether the previous maximum displacement data is the peak displacement based on a difference between the previous and current maximum displacement data.

21. The system of claim 19, wherein the processor is configured to determine a timing shift direction of the tracking pulses based upon the previous and current maximum displacement data and configured to adjust the timing of the tracking pulses in the timing shift direction based on the previous and current maximum displacement data.

22. A non-transitory computer readable media comprising program instructions, which when executed by one or more processors measure a shear wave velocity in a tissue with an ultrasound system comprising:
 repeating a plurality of steps until one of displacement data indicative of displacement motion of the tissue at a sample position is determined as a peak displacement of the shear wave, wherein each repetition of the steps comprises:
 applying a pushing pulse to a displacement origin within the tissue;
 generating the shear wave in response to the pushing pulse;
 sampling the displacement data by a plurality of tracking pulses; and
 adjusting a timing of at least one of the tracking pulses relative to the pushing pulse by causing samplings from different occurrences of the pushing pulse to differ from each other so as to obtain more sample points demonstrating a temporal displacement motion of the shear wave at the sample position; and
 calculating the shear wave velocity based upon the peak displacement.

* * * * *